United States Patent
Biedermann

(10) Patent No.: US 11,583,320 B2
(45) Date of Patent: Feb. 21, 2023

(54) IMPLANT FOR BONES OR VERTEBRAE WITH SELF-CONSTRAINED FLEXIBILITY

(71) Applicant: BIEDERMANN TECHNOLOGIES GMBH & CO. KG, Donaueschingen (DE)

(72) Inventor: Markku Biedermann, Miami, FL (US)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 204 days.

(21) Appl. No.: 16/804,576

(22) Filed: Feb. 28, 2020

(65) Prior Publication Data

US 2020/0261121 A1   Aug. 20, 2020

Related U.S. Application Data

(63) Continuation of application No. 16/113,259, filed on Aug. 27, 2018, now Pat. No. 10,610,266, which is a
(Continued)

(51) Int. Cl.
*A61B 17/86* (2006.01)
*A61B 17/70* (2006.01)
(Continued)

(52) U.S. Cl.
CPC ...... *A61B 17/7059* (2013.01); *A61B 17/7019* (2013.01); *A61B 17/7026* (2013.01);
(Continued)

(58) Field of Classification Search
CPC .............................................. A61B 17/86–869
See application file for complete search history.

(56) References Cited

U.S. PATENT DOCUMENTS

| 6,206,882 B1 | 3/2001 | Cohen |
| 6,989,011 B2 | 1/2006 | Paul |

(Continued)

FOREIGN PATENT DOCUMENTS

| CN | 1037451 A1 | 11/1989 |
| EP | 0 340 413 A1 | 3/1989 |

(Continued)

OTHER PUBLICATIONS

Chinese Office action and English translation for Application No. 201410363937.5, dated Jul. 19, 2017 (22 pages).
(Continued)

*Primary Examiner* — Eduardo C Robert
*Assistant Examiner* — Steven J Cotroneo
(74) *Attorney, Agent, or Firm* — Lewis Roca Rothgerber Christie LLP

(57) ABSTRACT

An implant for the stabilization of bones or vertebrae is provided, the implant being a solid body including a longitudinal axis that defines a longitudinal direction and including a flexible section that has a surface and has a length in the longitudinal direction, the flexible section including at least one cavity located near the surface and having a width in the longitudinal direction that is smaller than the length of the flexible section, the at least one cavity being connected to the surface through at least one slit, and a width of the slit in the longitudinal direction being smaller than the width of the cavity.

23 Claims, 7 Drawing Sheets

Related U.S. Application Data continuation of application No. 15/346,560, filed on Nov. 8, 2016, now Pat. No. 10,085,775, which is a continuation of application No. 14/447,441, filed on Jul. 30, 2014, now Pat. No. 9,522,019.

(60) Provisional application No. 61/860,719, filed on Jul. 31, 2013.

(51) Int. Cl.
| | |
|---|---|
| *A61B 17/80* | (2006.01) |
| *B22F 5/10* | (2006.01) |
| *B29C 64/153* | (2017.01) |
| *B22F 10/20* | (2021.01) |
| *B22F 3/24* | (2006.01) |
| *B22F 5/00* | (2006.01) |
| *B29K 105/00* | (2006.01) |
| *B29L 31/00* | (2006.01) |
| *A61B 17/00* | (2006.01) |
| *B29K 71/00* | (2006.01) |

(52) U.S. Cl.
CPC ...... *A61B 17/7028* (2013.01); *A61B 17/7031* (2013.01); *A61B 17/80* (2013.01); *A61B 17/8085* (2013.01); *A61B 17/866* (2013.01); *A61B 17/8625* (2013.01); *B22F 3/24* (2013.01); *B22F 5/106* (2013.01); *B22F 10/20* (2021.01); *B29C 64/153* (2017.08); *A61B 17/869* (2013.01); *A61B 2017/00862* (2013.01); *B22F 2003/245* (2013.01); *B22F 2005/004* (2013.01); *B29K 2071/00* (2013.01); *B29K 2105/251* (2013.01); *B29K 2871/00* (2013.01); *B29K 2995/0056* (2013.01); *B29L 2031/7532* (2013.01); *Y02P 10/25* (2015.11)

(56) References Cited

U.S. PATENT DOCUMENTS

| | | | |
|---|---|---|---|
| 7,621,912 B2 | 11/2009 | Harms et al. | |
| 7,744,631 B2 * | 6/2010 | Perez-Cruet | A61B 17/7025 606/253 |
| 9,522,019 B2 | 12/2016 | Biedermann | |
| 11,007,347 B2 * | 5/2021 | Algawi | A61M 25/0662 |
| 11,224,467 B2 * | 1/2022 | Peterson | A61B 17/863 |
| 2005/0085815 A1 | 4/2005 | Harms et al. | |
| 2005/0154390 A1 * | 7/2005 | Biedermann | A61B 17/7035 606/279 |
| 2009/0062868 A1 * | 3/2009 | Casutt | A61B 17/7001 606/301 |
| 2009/0157123 A1 | 6/2009 | Appenzeller et al. | |
| 2011/0144703 A1 * | 6/2011 | Krause | A61B 17/869 606/309 |
| 2012/0053640 A1 | 3/2012 | Trieu | |
| 2012/0130381 A1 * | 5/2012 | Germain | A61B 17/1642 606/84 |
| 2012/0191208 A1 | 7/2012 | Olson | |
| 2015/0012048 A1 * | 1/2015 | Huebner | A61B 17/8685 606/304 |
| 2015/0147722 A1 * | 5/2015 | Tsai | A61C 8/0018 606/62 |
| 2016/0045198 A1 * | 2/2016 | Bachrach | A61B 17/82 606/151 |
| 2017/0189085 A1 * | 7/2017 | Krause | A61B 17/7208 |

FOREIGN PATENT DOCUMENTS

| | | |
|---|---|---|
| EP | 1 221 308 A1 | 7/2002 |
| FR | 2 728 454 A1 | 6/1996 |
| WO | WO 00/23014 | 4/2000 |
| WO | WO 2004/105577 A2 | 12/2004 |
| WO | WO 2006/110795 A1 | 10/2006 |
| WO | WO 2012/100054 A1 | 7/2012 |
| WO | WO 2013/018062 A1 | 2/2013 |

OTHER PUBLICATIONS

European Search Report from European Application No. EP 13 19 0622.4, filed Oct. 29, 2013, European Search Report dated May 12, 2014 and dated May 27, 2014 (16 pgs.).

* cited by examiner

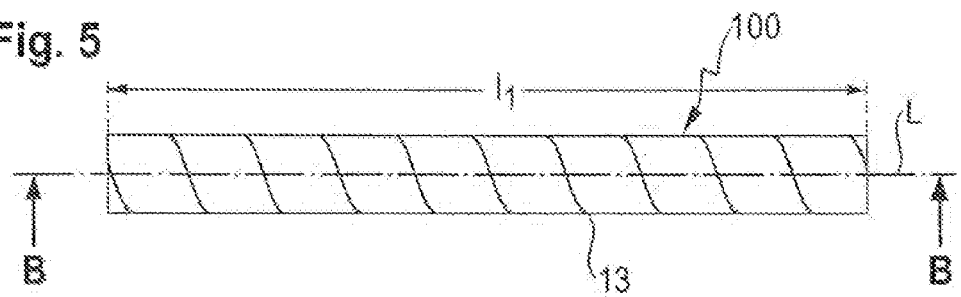
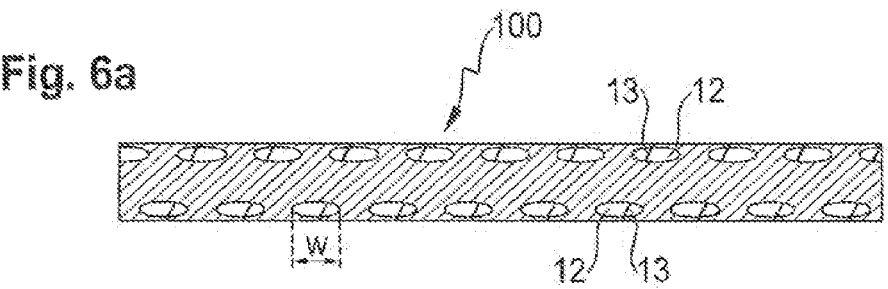
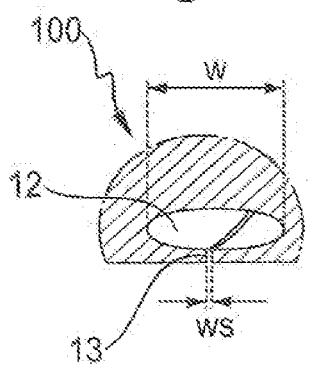 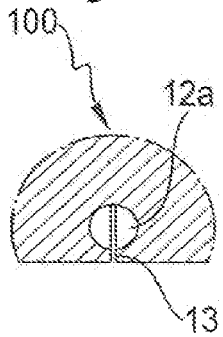 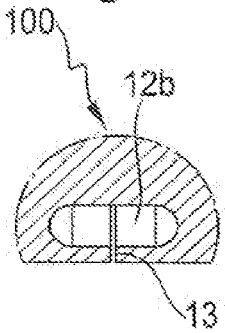 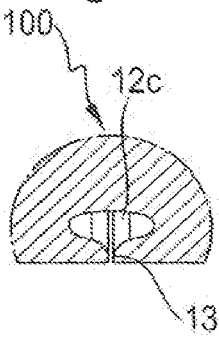
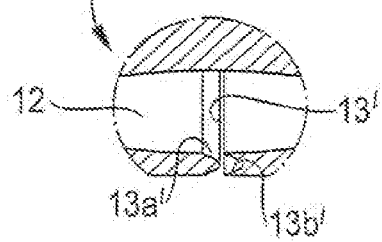 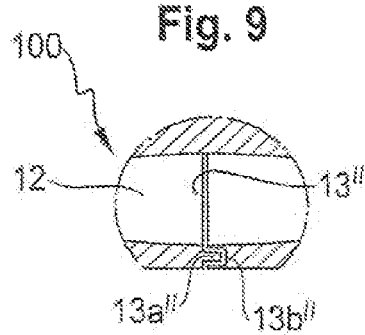

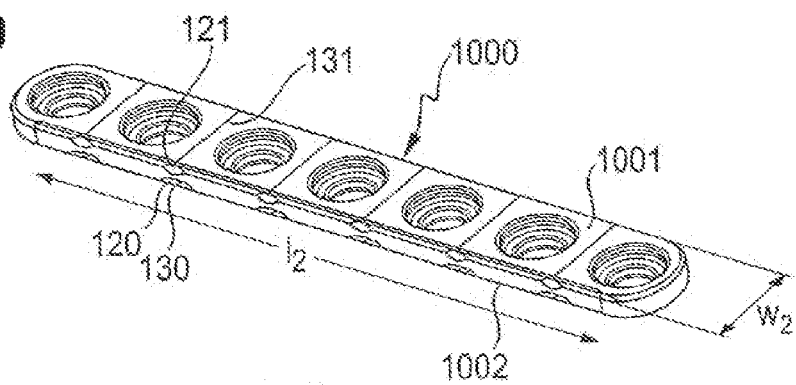
Fig. 10
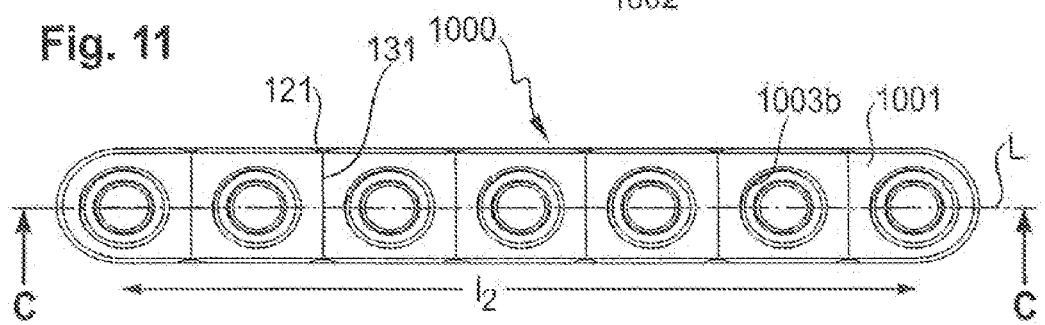
Fig. 11
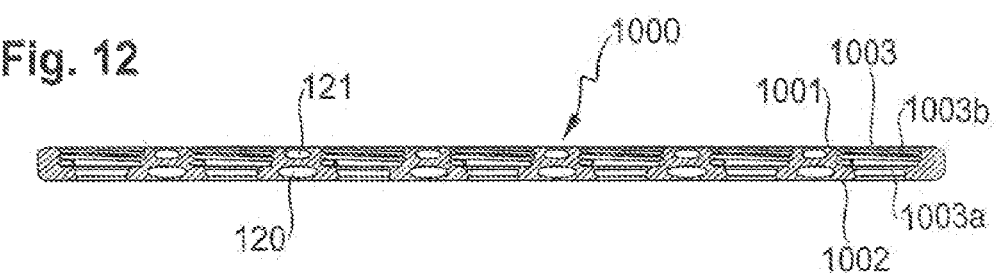
Fig. 12
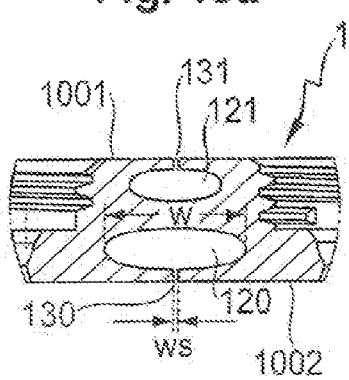 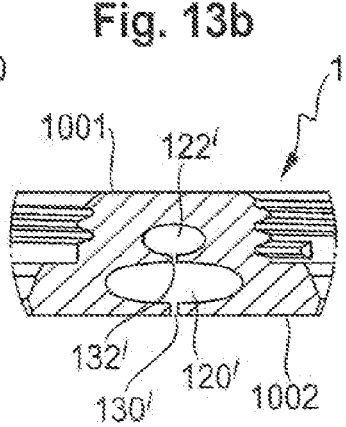 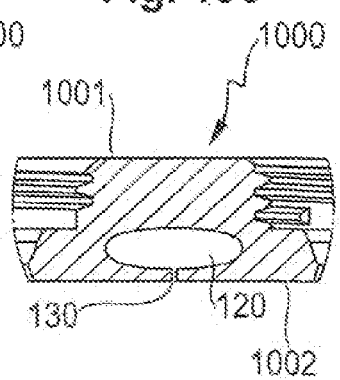
Fig. 13a   Fig. 13b   Fig. 13c

IMPLANT FOR BONES OR VERTEBRAE WITH SELF-CONSTRAINED FLEXIBILITY

CROSS-REFERENCE TO RELATED APPLICATION

This application is a continuation of U.S. patent application Ser. No. 16/113,259, filed Aug. 27, 2018, which is a continuation of U.S. patent application Ser. No. 15/346,560, filed Nov. 8, 2016, now U.S. Pat. No. 10,085,775, which is a continuation of U.S. patent application Ser. No. 14/447,441, filed Jul. 30, 2014, now U.S. Pat. No. 9,522,019, which claims the benefit of U.S. Provisional Patent Application Ser. No. 61/860,719, filed on Jul. 31, 2013, the disclosures of each of which are hereby incorporated by reference.

BACKGROUND

The invention relates to a flexible implant for the stabilization of bones or vertebrae, wherein the implant is formed as a solid body that has at least one cavity located near the surface wherein the cavity is connected to the surface through at least one slit and wherein a width of the slit is smaller than a width of the cavity. The slit is configured to narrow when the implant is flexed, and the closing of the slit during flexion limits the extent of flexion of the implant. The implant may be realized, for example, as a bone screw, a stabilization rod, or a bone plate.

Dynamic stabilization devices are known, in which the bone parts or vertebrae to be stabilized are able to carry out a controlled limited motion relative to each other. For example, a rod-shaped implant for the connection of bone anchoring elements that includes at least one rigid section that is configured to be placed in a receiver member of a bone anchoring element and a flexible section that is adjacent to the rigid section and wherein the flexible section and the rigid section are formed as a continuous one-piece element is known from U.S. Pat. No. 7,621,912 B2.

An elastic or flexible element for use in a stabilization device for bones or vertebrae in the form of a helical spring is known from US 2005/0154390 A1. The flexible element can be part of the shaft of a flexible bone screw or of a stabilization rod or a plate.

Such known flexible implants include a longitudinal bore and a helical slot-shaped opening in the wall. The flexibility is determined by the geometry of the hollow bore and the helical slot-shaped opening. To limit the flexibility or strengthen the implant, a core may be provided in the hollow bore. The flexible characteristics of the known devices can be precisely designed by the geometry of the helical slot-shaped opening and the dimensions of the hollow bore and optionally the core inserted therein. However, such implants sometimes do not have a limitation of the flexibility, or a limitation of the flexibility to a certain degree requires a more complex design in terms of the number of parts or the materials used. Therefore, there remains a need for a further improved flexible implant.

SUMMARY

According to an aspect of embodiments of the present invention, a flexible implant has an improved strength and is easy to manufacture.

The implant is an elongate solid body that obtains flexibility by a plurality of cavities or cavity portions near the outer surface that are connected to the surface through a slit. Such a monolithic structure leads to lower production costs, since no assembly is required. The stiffness can be designed and controlled by the geometric design as opposed to relying on exotic and costly materials. The implant can be manufactured using electrical discharge machining (EDM), such as wire cutting, and/or an additive manufacturing technology, such as, for example, Selective Laser Sintering using a metallic or plastic powder material.

The monolithic structure provided by the solid body provides a degree of flexibility and dynamic motion while simultaneously exhibiting sufficient strength. In particular, it is possible to provide a thin elongate implant that has a smaller core diameter compared to elongate implants with a hollow interior, or, if it has substantially the same diameter as an implant with hollow interior, shows less bending. The implant according to aspects of some exemplary embodiments may be a bone screw, a stabilization rod, or a bone plate. However, it can be any other implant that is required to have flexible characteristics.

According to another aspect, the implant has substantially the same strength and/or volume or diameter as a conventional non-flexible implant, but exhibits a micro-motion due to its structure with inherent flexibility.

The motion of the implant can be constrained by a built-in geometric design that allows movement with an elastic loading curve until a limit is reached. This limit may be created by surfaces provided at the implant that contact each other so that further flexion is prevented or constrained. Because the flexibility of the implant is self-constrained, an external geometry to provide this limit is not required.

According to another aspect, a tension side of the implant is defined as the side where load is applied to the implant in a transverse direction, and a compression side of the implant is defined as the side of the implant that is compressed when the load is applied in the transverse direction. The at least one cavity includes a structure that forms a first stop to limit the flexion of the implant on the compression side and/or a second stop to limit the tensile strain and flexion on the tension side. Via the second stop, forces can be transmitted also via the tension side.

According to another aspect, two or more stiffness zones may be designed depending on the desired application. In addition, the size and shape of the cavities may be designed such that load peaks acting onto the implant during flexion that could cause cracks in the implant body are prevented.

In a further embodiment, a longitudinal implant has a self-constrained torsional flexibility. Further, it is also possible to have an implant with two or more stiffness zones with regard to torsional loads.

BRIEF DESCRIPTION OF THE DRAWINGS

Further features and advantages will become apparent from the description of some embodiments together with the accompanying drawings.

FIG. 5 shows a side view of an implant according to a second embodiment in the form of a stabilization rod.

FIG. 6a) shows a cross-sectional view of the stabilization rod shown in FIG. 5 along line B-B in FIG. 5.

FIG. 6b) shows an enlarged view of a detail of FIG. 6a).

FIGS. 7a) to 7c) show an enlarged cross-sectional view of modifications of the shape of the cavity shown in FIG. 6a).

FIG. 8 shows an enlarged cross-sectional view of a modification of the design of the slit shown in FIG. 6a).

FIG. 9 shows an enlarged cross-sectional view of a further modification of the design of the slit shown in FIG. 6a).

FIG. 10 shows a third embodiment of the implant in the form of a bone plate.

FIG. 11 shows a top view of the bone plate of FIG. 10.

FIG. 12 shows a cross-sectional view of the bone plate of FIG. 11 along line C-C in FIG. 11.

FIGS. 13a) to 13c) show enlarged views of various modifications of the cavities in the bone plate.

DETAILED DESCRIPTION

Figure 1:
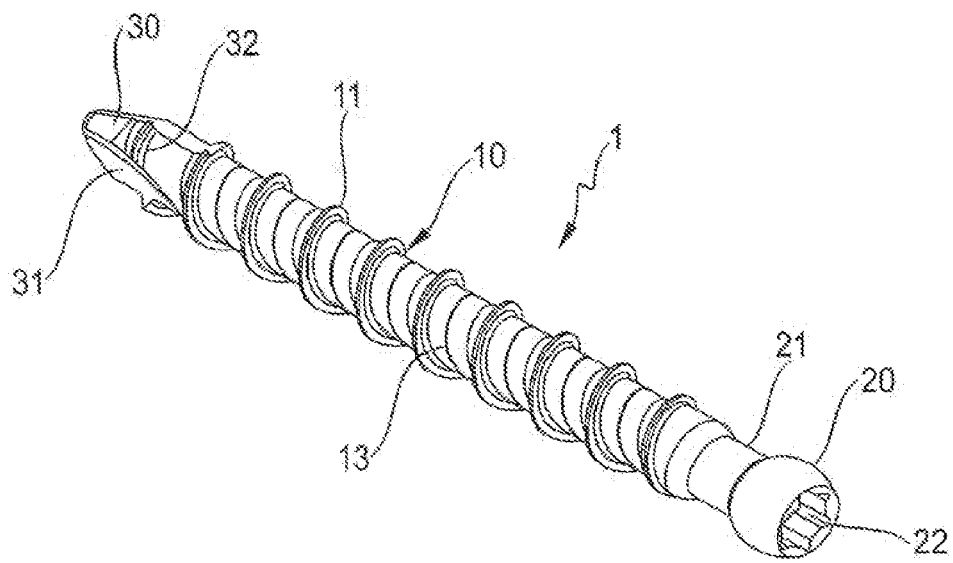
FIG. 1 shows a perspective view of an implant according to a first embodiment which is in the form of a bone screw.
Figure 2:
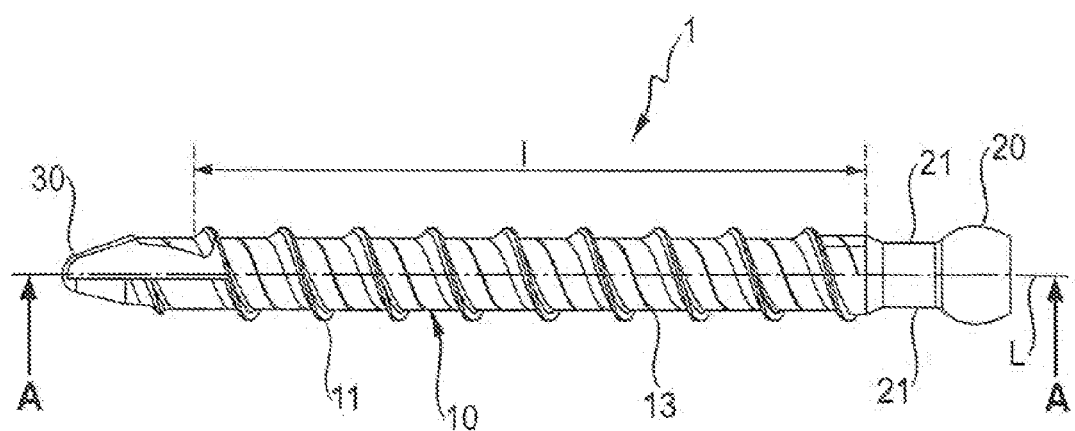
FIG. 2 shows a side view of the bone screw shown in FIG. 1.
Figure 3A:
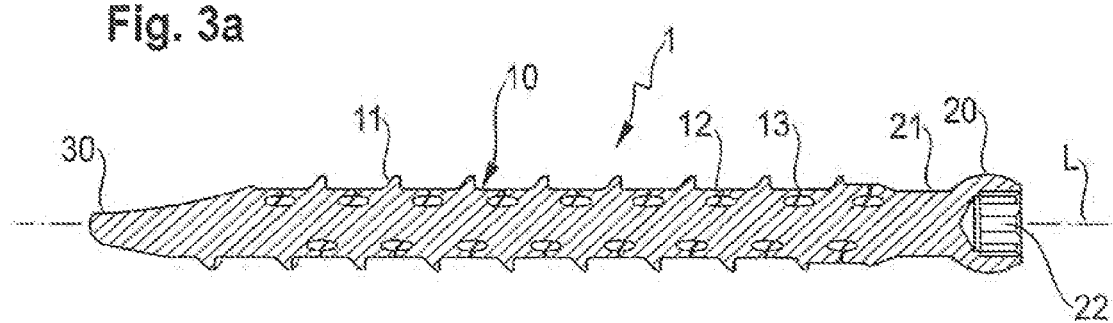
FIG. 3a) shows a cross-sectional view of the bone screw shown in FIG. 2 along line A-A in FIG. 2.

A first embodiment of the implant will be described with reference to FIGS. 1 to 4b). The implant is a bone screw 1 that comprises a shank 10 with a bone thread 11 in at least a portion thereof, a head 20 at one end, a tip 30 at the opposite end of the shank 10, and a longitudinal axis L that forms the screw axis. Referring in particular to FIGS. 3a) and 3b), the portion of the shank 10 that is provided with the bone thread 11, i.e. the bone thread portion, has an outer surface and a length 1. The bone screw 1 is formed as a monolithic, solid body. In particular, it has a solid, non-cannulated interior. At a distance from the outer surface a cavity 12 is formed that extends in a helical path around the longitudinal axis L of the bone screw over the length 1 of the bone thread portion. The spinning direction of the helical cavity 12 is the same as the direction of the bone thread 11.

Figure 3B:
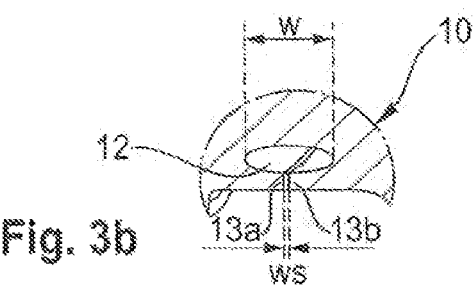
FIG. 3b) shows an enlarged view of a detail of FIG. 3a).

The cavity 12 has an oval-shaped cross-section in a cross-sectional plane containing the longitudinal axis L, as shown in FIGS. 3a and 3b. A width w of the cavity 12 in the direction of the longitudinal axis L is smaller than the length 1 of the bone thread portion.

The width w of the cavity 12 in the longitudinal direction is furthermore such that it is smaller than a thread pitch, i.e. the distance between the crests of the bone thread 11 in the longitudinal direction. As can be seen in particular in FIG. 3a), the cavity 12 is located at a position that corresponds to the root of the bone thread 11. Furthermore, the cavity 12 is open to the outer surface of the shank 10 by means of a slit 13 that extends in a helical manner around the longitudinal axis L as can be seen in particular in FIGS. 1 and 2. The slit 13 comprises opposing surfaces 13a and 13b and a width ws that is the distance between the opposing surfaces 13a and 13b.

The slit 13 opens into the cavity 12 at a position that corresponds substantially to the center of the cavity 12 in a longitudinal direction. By this design, the helically-shaped cavity 12 exhibits a plurality of cavity portions in a cross-sectional view, as shown in FIG. 3a), that are separated from each other in the longitudinal direction by the solid body of the bone screw 1. The width ws of the slit 13 is smaller than the width w of the cavity 12 in a longitudinal direction. More specifically, the slit 13 has such a size that the shank portion between the cavity 12 and the outer surface that is on both sides of the slit 13 is thinned. Therefore, the screw is flexible in the region of the cavity 12. The length of the slit 13 in the transverse direction is such that the cavity 12 is located in an outer half of the radius of the shank 10. More specifically, seen in a radial direction, the cavity 12 is closer to the outer surface than to the longitudinal axis L.

The tip 30 of the bone screw may be a self-cutting tip. The self-cutting tip 30 comprises bone-thread free sections 31 that extend in a slightly twisted manner from the outermost portion of the tip 30 into the shank, thereby creating cutting edges 32. Furthermore, between the head 20 and the bone thread portion of the shank 10, there may be a neck portion 21. The head 20 shown in the embodiment is a spherically-segment shaped head 20 and comprises an engagement portion 22 for a tool.

The bone screw 1, in an exemplary embodiment, is made from a biocompatible metal or a biocompatible metal or metal alloy such as stainless steel, titanium, or a nickel-titanium alloy. In particular, alloys having superelasticity such as Nitinol or superelastic β-titanuim alloys are suitable. The bone screw 1 can also be made from a biocompatible plastic material, such as, for example, from PEEK (polyetheretherketone).

To obtain the monolithic, solid structure, the bone screw 1, in an exemplary embodiment, is manufactured using an additive manufacturing method, such as Selective Laser Sintering (SLS), Selective Laser Melting, or electron beam melting. With such a method, it is possible to fabricate the internal cavities 12 into the solid body and the slit 13 during the layer-wise build-up of the implant based on computer data defining the shape and size of the implant. When using Selective Laser Sintering or Selective Laser Melting, laser sinterable metals or metal alloys or laser sinterable plastic materials are used, for example, laser sinterable titanium powder or laser sinterable stainless steel powder or laser sinterable PEEK powder.

In a modified method of manufacturing, the solid body with the internal cavities is made by an additive manufacturing method, in particular by SLS, while the slits remain still closed. Thereafter, the slits are cut using a conventional technique such as wire cutting.

Figure 4A:
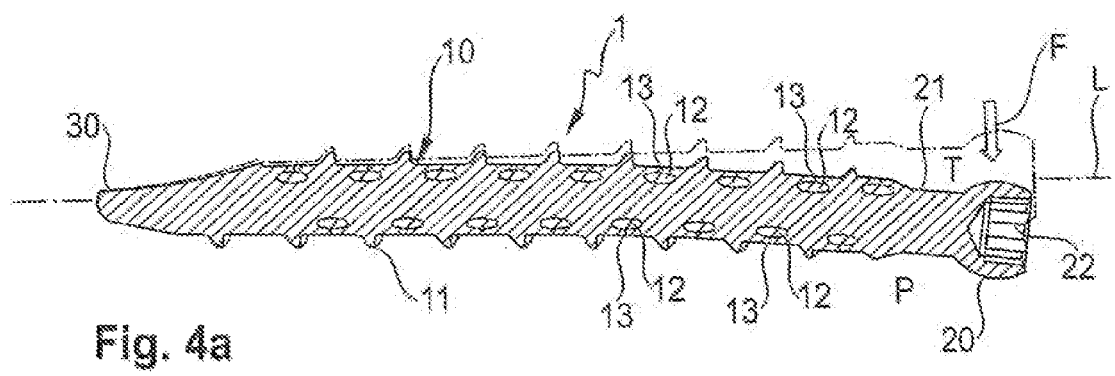
FIG. 4a) shows a cross-sectional view of the bone screw shown in FIG. 2 along line A-A in FIG. 2 wherein a force acts onto the bone screw that deflects the bone screw in a transverse direction.
Figure 4B:
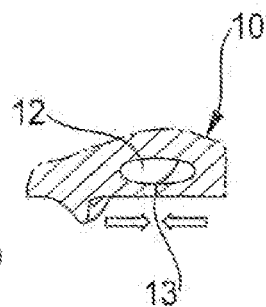
FIG. 4b) shows an enlarged view of a detail of FIG. 4a).
Figure 14:
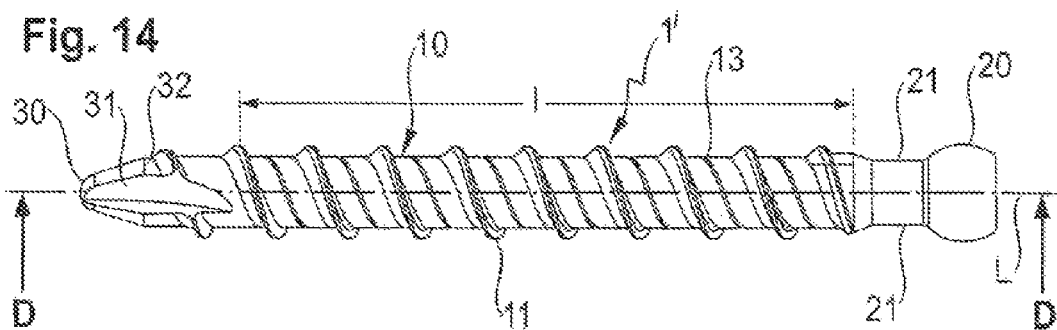
FIG. 14 shows a side view of an implant according to a fourth embodiment which is in the form of a bone screw.

In use, when a force F that is directed transverse to the longitudinal axis L acts onto the bone screw 1, the bone screw 1 is flexible in a direction transverse to the longitudinal direction, as can be seen in FIG. 4a). The side where the load is applied in the transverse direction is defined as a tension side T of the implant. The cavity 12 and the slit 13 that is connected to the cavity 12 allow the bone screw to bend, thereby moving the opposing surfaces 13a, 13b of the slit 13 towards each other. The side where the implant is compressed is defined as a compression side P of the implant. When the opposing surfaces 13a, 13b abut against each other forming a stop, whereby the slit 13 is closed, as shown in FIG. 4b), the bone screw 1 is constrained in view of further bending. Thus, the stop created by the opposing surfaces 13a, 13b of the slit acts as a limit for the pressure applied to the bone screw transverse to the longitudinal direction. The stiffness is controlled by the geometric design, such as the width and the volume of the cavity 12 and the length and width of the slit 13. The stop provided by the abutting surfaces 13a, 13b of the slit 13 provides a self-constraining characteristic to the bone screw 1. Therefore, no external or separate part that provides a flexibility constraining effect is required. Due to the helical structure of the cavity 12, bending of the bone screw is constrained in view of all directions perpendicular to the longitudinal axis L.

Because the bone screw 1 is manufactured from a solid body and does not comprise a central longitudinal bore, the strength of the bone screw 1 may be greater than that of known flexible bone screws that comprise a spring element for providing the flexibility. This reduces a risk of failure due to cracking. Because the strength is increased, it may be possible to manufacture the bone screw 1 with a smaller core diameter compared to flexible implants with a hollow interior. Due to its structure, the implant has at least two stiffness zones in a load versus displacement curve. An initial lower stiffness due to the possible micro-motion, that resembles the stiffness of an implant with a smaller diameter and a subsequent higher stiffness that resembles the stiffness of an implant with a greater diameter. For example, a bone screw of a core diameter of $X_1$, for example 7 mm, may have initially the lower stiffness of a bone screw with a core diameter of $X_2<X_1$, for example 3.5 mm, when the gaps are not yet closed, and may have subsequently upon further bending the greater stiffness of a bone screw with a core diameter of $X_1$ when the slit is closed.

The bone screw may be used, for example, as a pedicle screw. In this case, it can be connected to a receiving part to form a polyaxial or a monoplanar bone anchor. For the receiving part, all kinds of receiving parts can be used that allow to pivotably hold the head of the bone screw and connect the bone screw to a spinal stabilization rod. When the vertebrae move, transverse forces may act on the pedicle screw. Due to its flexibility, the pedicle screw can bend and thus prevent fracture of weak bone material.

Further modifications of the embodiments described may be contemplated. For example, the bone screw is not limited to the embodiment shown. For example, the bone screw may have a non-self-cutting tip, and/or it may have a different head, such as a lens-shaped head or a disc-shaped head or any other head. It may even be provided without a head. The bone screw may also be used together with a bone plate.

A second embodiment of the implant will be described with reference to FIGS. 5 and 6. Parts or portions that are identical or similar to the first embodiment are referenced using the same reference numerals. The implant in this case is a stabilization rod 100, such as for the stabilization of the spinal column, for example. The rod 100 is made as a monolithic, cylindrical solid body having a cylinder or longitudinal axis L, a surface and a length $l_1$. As in the first embodiment, a cavity 12 is extending in a helical fashion around the longitudinal axis L at a distance from the surface of the rod 100. The cavity 12 has, as in the first embodiment, an oval-shaped cross-section in a plane containing the longitudinal axis L, as can be seen in FIGS. 6a) and 6b). The cavity 12 opens to the surface via a slit 13, as in the first embodiment, the width ws of the slit being smaller than the width w of the cavity 12 in the longitudinal direction. In particular, the width ws is such that, as seen in the cross-sectional view of FIG. 6a), a plurality of cavity portions are arranged near the surface and extend in longitudinal direction, which are separated by solid portions of the rod 100. The cavity 12 and the slit 13 may extend along the full length of the rod or along a portion of the rod. The geometry of the cavity 12 and of the slit 13 may vary along the longitudinal direction of the rod to generate different portions with different stiffness. The pitch of the helix may be the same or may vary along the length of the rod.

The rod 100 may be manufactured through a manufacturing method as described above with respect to the bone screw 1, such as an additive manufacturing method, such as Selective Laser Sintering.

The rod may be used to connect two bone anchoring devices, for example two pedicle screws screwed into the pedicles of adjacent vertebrae. Due to the flexible characteristics of the rod 100 based on the helically-shaped cavity 12 with the helically-shaped slit 13, the rod 100 permits a controlled motion of the adjacent vertebrae. The motion is limited by the self constrained flexibility of the rod 100.

Referring to FIGS. 7a) to 7c), various modifications of the cavity 12 are shown. As shown in FIG. 7a) a cavity 12a may have a circular cross-section. A reduced volume of the cavity may lead to a higher torsional stiffness. As shown in FIG. 7b), a cross-section of a cavity 12b may be an elongate oval shape with straight long sides, which resembles the cross-section of a capsule. The width w of the cavity 12b with this design is enlarged, resulting in an enhanced bending flexibility. As shown in FIG. 7c), a cross-section of a cavity 12c may have an inverted drop-shape wherein the drop-shape has a flattened end portion. The various modifications of the shape of the cavity can be used for the rod 100 as well as for the bone screw 1. For a given geometry and size of an implant, it is possible to use various modifications of the shape and volume of the cavity and also the slits in order to design an implant with a particular behavior, for example, with a specific torsional and bending stiffness.

Referring to FIGS. 8 and 9, modifications of the design of the slit are shown. FIG. 8 shows a first example of a modification of the slit with an interlocking design. A slit 13' comprises opposing side walls 13a', 13b' that exhibit a V-shape in a cross-sectional view so that the side wall 13a' forms a projection and the side wall 13b' forms a groove into which the projection fits and interlocks therewith when a force acts onto the implant such that a distance between opposing surfaces of the opposing side walls 13a', 13b' is decreased.

FIG. 9 shows a further modification of the design of the slit with an interlocking feature. A slit 13" comprises opposing side walls 13a", 13b" that have a rectangular cross-section when seen in a cross-sectional view. Hence, the side wall 13a" forms a projection and the side wall 13b" forms a groove, and the projection fits into the groove. The examples shown in FIGS. 8 and 9 having interlocking designs provide for a more precise adjustment of the flexibility constraining stop. In addition, the interlocking designs provide a safety means that prevents the two sides of the slit from sliding along each other if the bending load is increased. It can be used with the implant in the form of a bone screw 1 according to the first embodiment or with the implant in the form of a stabilization rod 100 according to the second embodiment.

A third embodiment of the implant will be described with reference to FIGS. 10 to 13*a*). The implant is a bone plate 1000 that comprises an upper surface 1001 and an opposite lower surface 1002 that faces the bone surface when the bone plate is used. The bone plate 1000 has a length l2 along which it is substantially straight and a width $w_2$ and may be of a rectangular shape with rounded ends with a longitudinal axis L. However, many different designs of bone plates may be contemplated as well. The bone plate 1000 further comprises at least two holes 1003 extending from the upper surface 1001 to the lower surface 1002. The holes 1003 may be provided with a seat 1003*a* for a bone screw (not shown) and an internal thread 1003*b* for a locking cap (not shown).

In the embodiment shown, a plurality of first cavities 120 is provided, and the first cavities 120 may extend along the width (e.g., the entire width) from one side to the opposite side of the bone plate 1000. The first cavities 120 are arranged near the lower surface 1002 and open into the lower surface 1002 through slits 130 as shown in FIG. 13*a*). The first cavities 120 have a straight shape in a direction perpendicular to the longitudinal direction and, in a cross-sectional view as shown in FIG. 12, an oval-shaped cross-section. Near the upper surface 1001, there are second cavities 121 that are arranged opposite to the first cavities 120 and open into the upper surface 1001 via slits 131 as shown in FIG. 13*a*). The second cavities 121 may have the same size and the same shape as the first cavities 120 or may have a different size and shape. In the example shown, the second cavities 121 are smaller than the first cavities 120 thereby rendering the flexibility of the bone plate 1000 in view of bending into the upper direction smaller than the flexibility in view of bending into the lower direction. The first and second cavities 120, 121 are arranged at positions between the holes 1003.

As in the previous embodiments, the size, shape, number and position of the cavities 120, 121 and the slits 130 determine the flexible characteristics of the bone plate 1000. Hence, by selecting the appropriate design, position and number of the cavities, the bone plate can be rendered flexible according to specific requirements.

FIGS. 13*b*) and 13*c*) show further modifications of the design of the bone plate. In FIG. 13*b*), third cavities 122' are provided upon first cavities 120' in a transverse direction and are connected to the first cavities 120' by slits 132'. The size and shape of the third cavities 122' and of the corresponding slits 132' may be, for example, smaller than that of the first cavities 120' and corresponding slits 130'. In the shown embodiment, the width of the first slit 130' is larger than the width of the third slit 132'.

With the design according to FIG. 13*b*) two stiffness zones are created by the first cavities 120' and by the third cavities 122', respectively. When a transverse force acts onto the bone plate, an initial contact is made by the opposing surfaces of the third slit 132' and, upon further bending, a secondary contact is established between the opposing surfaces of the first slit 130'.

Providing cavities 120 only on one side, for example near to the lower surface 1002 as shown in FIG. 13*c*), allows a constrained flexibility in one direction only.

The bone plate 1000 may be manufactured using a conventional manufacturing process. That means, also the cavities and the slits can be manufactured using a conventional manufacturing process, such as electrical discharge machining (EDM). This is possible because the cavities have a straight configuration. Alternatively, or in addition, additive manufacturing methods, such as Selective Laser Sintering may be used also to manufacture the bone plate 1000.

Also, for embodiments of the bone plate, the modified design of the cavities as shown in FIGS. 7*a*) to 7*c*) and/or the modified design of the slits as shown in FIGS. 8 and 9 can be used.

Figure 15A:
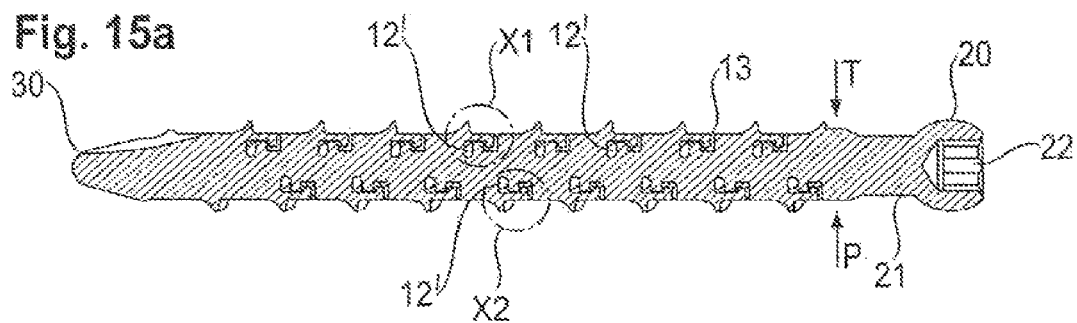
FIG. 15a) shows a cross-sectional view of the bone screw shown in FIG. 14 along line D-D in FIG. 14.

A fourth embodiment of the implant in the form of a bone screw 1' will be described with reference to FIGS. 14 to 16*b*). Parts and portions that are identical or similar to the above described embodiments are marked with the same reference numerals and the description thereof is not repeated. The bone screw 1' differs from the bone screw 1 according to the first embodiment in the design of the cavity. The cavity 12' is composed of several sections that are formed by the inner wall of the cavity 12'. The first section comprises the slit 13 that extends in a cross-sectional view as shown in FIGS. 15*a*) and 15*b*), substantially perpendicular to the longitudinal axis L and that is open to the surface. The wall of the cavity 12' in the section comprising the slit 13 forms the two opposing wall portions 13*a*, 13*b* as in the first embodiment, the distance between which defines the width ws of the slit 13. As can be seen in particular in FIGS. 14 and 15*a*), the slit 13 opens to the surface at a position between the crests of the bone thread 11, i.e. in the root of the bone thread 11, and extends in a helical shape around the longitudinal axis L.

Figure 15B:
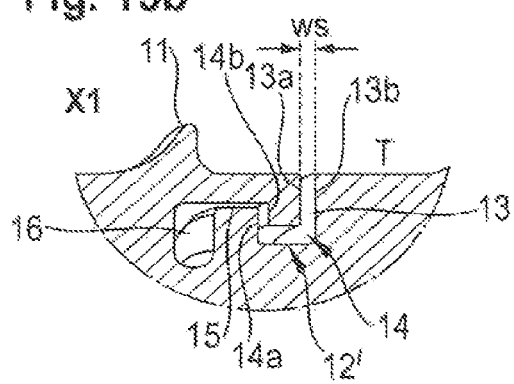
FIG. 15b) shows an enlarged view of a detail including a portion of the cavity in FIG. 15a) at the tension side.

Following the slit 13, the cavity 12' comprises a substantially L-shaped section 14, that has opposing wall portions 14*a*, 14*b* forming the bottom of the L-shape that are substantially parallel to the opposing wall portions 13*a*, 13*b* of the slit 13 in the cross-sectional view. The upper portion of the L-shaped section 14 that is adjacent to the slit 13 is connected to the slit 13. Seen as a whole, the slit 13 and the L-shaped section 14 of the cavity resemble a groove and a projection that engages the groove with a gap 14*c* between the bottom of the groove and the side walls of the groove on the one hand and the projection on the other hand. The gap 14*c* allows the projection to move within the groove. Following the L-shaped section 14, the cavity 12' comprises a substantially straight section 15 that extends substantially parallel to the longitudinal axis L. A width of the substantially straight section 15 in the longitudinal direction may be smaller than a width ws of the slit 13. Finally, the straight section 15 extends to an end section 16 that has a substantially oval-shaped cross section with its long sides substantially perpendicular to the longitudinal axis L. Seen in the cross-sectional view as shown in FIGS. 15*b*) and 15*c*), the course of the sections of the cavity resembles an S-shape, inverted S-shape or a double hook with substantially rectangular-segment, rounded edges. The end section 16 may have a greater width compared to the width ws of the slit 13 and provides space for compression. The orientation of the cavity 12' is from the slit 13 towards the tip 30 of the bone screw.

Also, in this embodiment, a width of the cavity 12' in the longitudinal direction is smaller than a length of the flexible section of the bone screw 1'.

The opposing wall portions 13a, 13b of the slit 13 form first opposing surfaces and provide a first stop at the compression side P when they are abutting against each other when the bone screw is flexed, as described below. The opposing wall portions 14a, 14b of the L-shaped section 14 form second opposing surfaces that provide a second stop when they are abutting against each other when the bone screw experiences tensile strain on the tension side T. In the longitudinal direction, the end section 16 of the cavity 12' may extend in the longitudinal direction until a position corresponding to a crest of the bone thread 11.

By the helical design of the cavity 12' as described above, the cavity 12' exhibits a plurality of cavity portions in a cross-sectional view, as shown in FIG. 15a), that are separated from each other in the longitudinal direction by the solid body of the bone screw 1'. In a radial or transverse direction, the cavity 12' is located in an outer half of the radius of the shank 10. More specifically, seen in the radial direction, the cavity 12' is located closer to the outer surface than to the longitudinal axis L.

Figure 15C:
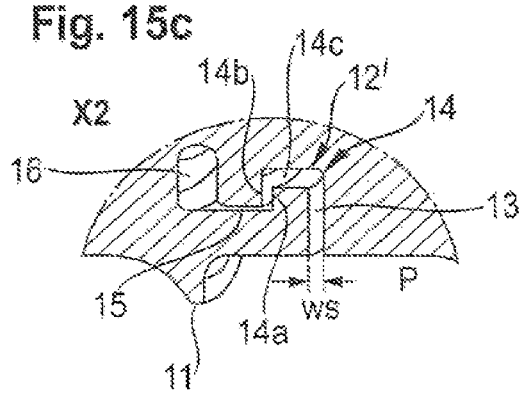
FIG. 15c) shows an enlarged view of another portion of the cavity shown in FIG. 15a) at the compression side.
Figure 16B:
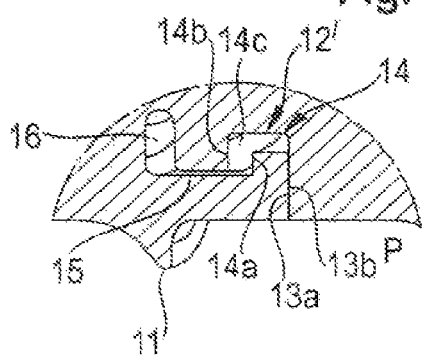
FIG. 16b) shows the cavity shown in FIG. 15c) when the transverse force acts onto the bone screw.

The function of the bone screw 1' in use will be described with reference to FIGS. 15b) to 16b). FIGS. 15b) to 16b) show enlarged views of a portion of the bone screw 1' of FIG. 15a) wherein the portion includes the cavity 12'. FIGS. 15b) and 15c) depict the cavity 12' in a condition in which no transverse force acts onto the bone screw 1'. Specifically, FIG. 15b) shows a portion of the cavity 12' that is on one side of the shank 10 and is marked in FIG. 15a) with X1. FIG. 15c) shows a portion of the cavity 12' that is arranged with the slit 13 opening to the opposite side of the shank 10 and that is marked in FIG. 15a) with X2. When no transverse force acts onto the shank 10, the shank 10 has a straight shape. The first opposing wall portions 13a, 13b do not contact each other and their distance corresponds to the distance ws of the slit 13. The second opposing wall portions 14a, 14b have a distance from each other and do not contact each other.

When a force F that is directed transverse to the longitudinal axis L acts onto the bone screw 1', the bone screw 1' is flexible in a direction transverse to the longitudinal direction.

Figure 16A:
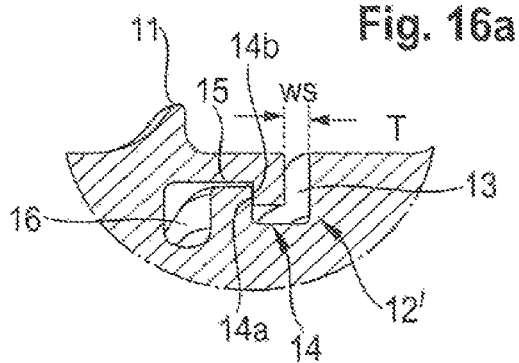
FIG. 16a) shows the cavity shown in FIG. 15b) when a transverse force acts onto the bone screw.

FIGS. 16a) and 16b) show a condition in which a transverse force F acts onto the bone screw 1' when load is applied on the tension side T. The cavity 12' allows the shank 10 to bend, thereby moving the opposing wall portions 13a, 13b of the slit 13 towards each other. When the opposing wall portions 13a, 13b abut against each other, the slit 13 is closed and a first stop is formed. The shank 10 is constrained in view of further bending. Thus, the first stop created by the opposing wall portions 13a, 13b of the slit 13 acts as a limit for the compression load applied to the bone screw 1' transverse to the longitudinal direction.

A second stop is provided by the abutment of the opposing wall portions 14a, 14b on the cavity portion that opens to the tension side T as shown in FIG. 16a). The abutment may take place simultaneously with the abutment of the opposing wall portions 13a, 13b, that form the first stop. Hence, the second stop prevents further bending that would increase the width of the slit 13 on the tension side. In addition, by means of the second stop, the force can also be transferred via the abutting surfaces 14a, 14b.

The stiffness of the implant is controlled by the geometric design, such as the volume of the cavity portions, the width of the slit 13 and the distance between the opposing wall portions 14a, 14b. The first stop and the second stop provided by the abutting opposing wall portions 13a, 13b and 14a, 14b provide a self-constraining characteristic to the implant. Therefore, no external or separate part that provides a flexibility constraining effect is required.

Figure 17:
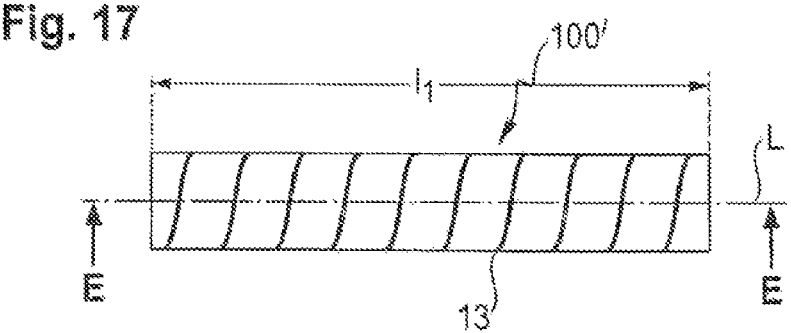
FIG. 17 shows a side view of an implant according to a fifth embodiment in the form of a stabilization rod.
Figure 18:
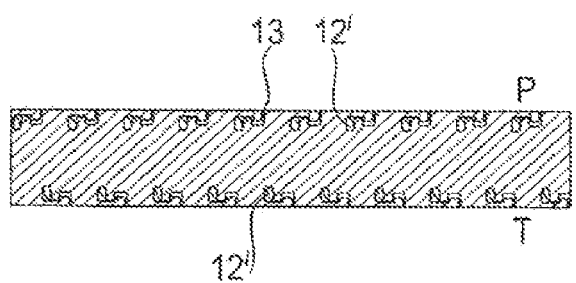
FIG. 18 shows a cross-sectional view of the stabilization rod shown in FIG. 18 along line E-E in FIG. 17.

A fifth embodiment of the implant in the form of a stabilization rod 100' will be described with reference to FIGS. 17 and 18. Parts or portions that are identical or similar to the previous embodiment are indicated with the same reference numerals. The rod 100' comprises the cavity 12' that has a shape identical or similar to the cavity 12' provided in the bone screw 1' according to the fourth embodiment. The geometry of the cavity 12' may vary along the longitudinal direction of the rod 100' to generate different portions having a different stiffness. The pitch of the helix may be the same or may vary along the length of the rod.

The rod may be manufactured through a manufacturing method as described above with respect to the rod 100, such as an additive manufacturing method, such as Selective Laser Sintering.

In use, the shape of the cavity 12' with the first opposing wall portions 13a, 13b and the second opposing wall portions 14a, 14b allows the rod to perform a constrained motion when a transverse load is applied.

Figure 19:
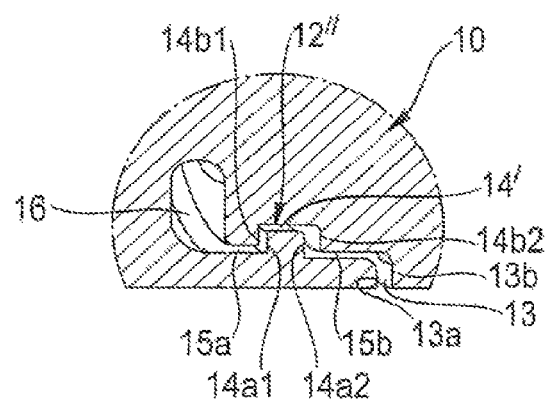
FIG. 19 shows an enlarged cross-sectional view of a modification of the shape of the cavity shown in FIGS. 14 to 18.

FIG. 19 shows a modified embodiment that is modified with regard to the shape of a cavity 12". Parts and portions that are identical or similar to the parts and portions of the cavity shown in the previous embodiment have the same reference numerals. The cavity 12" comprises the end portion 16 and the slit 13 as in the previous embodiment. Between the end portion 16 and the slit 13, there is a middle portion 14' that resembles a rectangular-segment or arc-shaped groove and projection configuration and a straight portion 15a, 15b at either end thereof that connects the middle portion 14' with the end portion 16 and the slit 13, respectively. A first stop, in this case, is provided by opposing side wall portions 14a2, 14b2 of the middle portion 14' that are closer to the slit 13, and a second stop is provided by opposing wall portions 14a1, 14b1 of the middle portion 14' that are closer to the end portion 16. The opposing wall portions 13a, 13b of the slit 13 can act as a third stop. In such a case, two stiffness zones may be provided at the compression side P. An initial contact is established by the first stop of the abutting surfaces 14a2, 14b2 and, upon further bending, a second contact is provided by the third stop.

The cavity 12' according to the fourth and the fifth embodiment or the modified cavity 12" may also be provided in a bone plate (not shown). The cavity 12' or 12" is arranged in the bone plate in a transverse direction and extends from one side to the other side similar to the cavity 120 in the bone plate 1000 shown in FIGS. 10 to 12. In order to limit the flexion also on the tension side, at least one cavity 12' or 12" is provided near the lower side 1002 of the bone plate and another cavity 12' or 12" is provided near the upper side 1001 of the bone plate. Such upper and lower cavities may be provided in a first arrangement at the same position in longitudinal direction of the bone plate or, in a second arrangement, may be offset from each other in the longitudinal direction. The second arrangement has an increased strength compared to the first arrangement.

Figure 20:
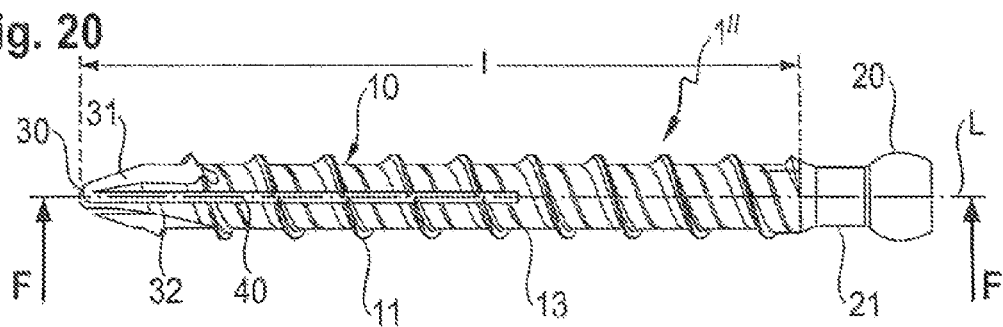
FIG. 20 shows a side view of an implant in the form of a bone screw according to a sixth embodiment.
Figure 21:
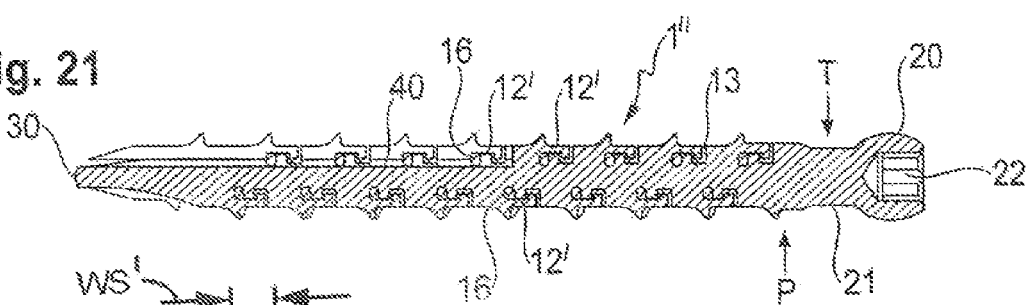
FIG. 21 shows a cross-sectional view of the bone screw shown in FIG. 20 along line F-F in FIG. 20.
Figure 22:
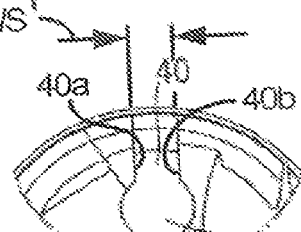
FIG. 22 shows an enlarged cross sectional view of a detail of FIG. 21.

An implant according to a sixth embodiment in the form of a bone screw 1" is shown in FIGS. 20 to 22. The bone screw 1" includes at least one of the cavity 12' and the slit 13 as described above with reference to the bone screw 1'. Alternatively, the bone screw 1" may include the cavity 12 described above with respect to the bone screw 1 or another configuration of the cavity and/or the slit described herein. To enhance the flexibility of the bone screw further, longitudinal slits 40 may be provided that extend from the outermost portion of the tip 30 into the shank 10. In the embodiment shown, the slits 40 are equidistantly arranged in a circumferential direction, and, for example, three or more slits 40 may be provided. The depth of the slits 40 in the radial direction corresponds substantially to a depth to which the end section 16 of the cavity 12' extends. The slits 40 have substantially rectangular cross-sections with opposing side walls 40a, 40b and a widened end portion 41, for example with a hollow cylinder segment-shaped inner wall and with an inner diameter w' that is greater than a width ws' of the outer portion of the slit 40 that is a distance between the opposing side walls 40a and 40b, as can be seen in FIG. 22. A width of the outer portion of the slit 40 may be smaller than a width of the cutting edges 32, as can be seen, for example, in FIG. 21. Furthermore, the slits 40 may extend up to the center of the shank 10 in the longitudinal direction. The dimensions and the number of the slits are not limited to the embodiment shown. The slits could be shorter or longer in the longitudinal direction, could have a greater or smaller depth and a greater or smaller width depending on the desired flexibility. In particular, the slits 40 can have a small width, similar to that of the helical slit 13 and the widened portion 41 is a cavity that can act as the cavity of the previous embodiments. With this design, the bending and torsional stiffness of the implant can be influenced.

Figure 23:
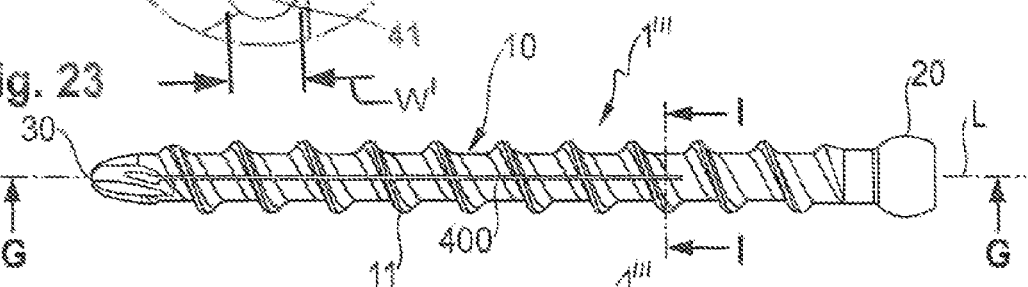
FIG. 23 shows a side view of an implant in the form of a bone screw according to a seventh embodiment.
Figure 24:
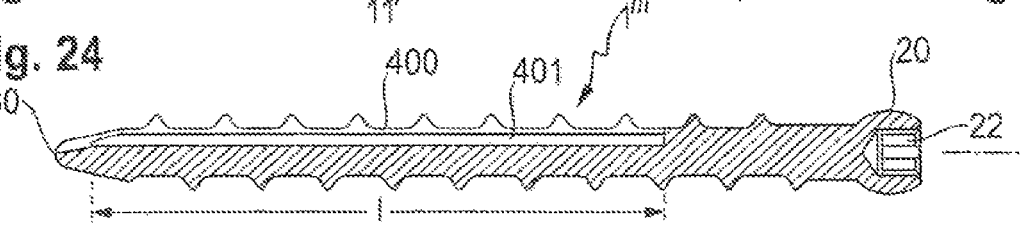
FIG. 24 shows a cross-sectional view of the bone screw shown in FIG. 23 along line G-G in FIG. 23.
Figure 25:
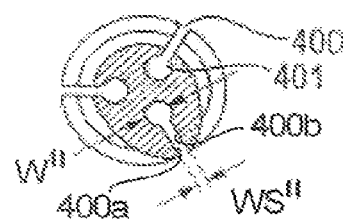
FIG. 25 shows an enlarged cross-sectional view of the bone screw shown in FIG. 24 along line I-I in FIG. 23.

A seventh embodiment of an implant will be described with reference to FIGS. 23 to 25. The implant is in the form of a bone screw 1''' comprising a head 20, a tip 30 and a shank portion 10 with a bone thread 11. The bone screw does not have the helical cavity and the helical slit as described with respect to the previous embodiments. Instead, the bone screw 1''' comprises longitudinal slits 400 that extend from the outermost portion of the tip 30 into the shank 10. In the embodiment shown, the slits 400 are equidistantly arranged in a circumferential direction and three slits 400 are provided. The slits 400 have substantially rectangular cross-sections with opposing side walls 400a, 400b and a widened end portion 401, for example with a hollow cylinder segment-shaped inner wall and with an inner diameter w" in the transverse direction that is greater than a width ws" of the outer portion of the slit 400 in the transverse direction that is a distance between the opposing side walls 400a and 400b, as can be seen in FIG. 25. The widened portion 401 forms a cavity.

The end portions 401 of the slits 400 may be drilled from the side of the tip into the shank in a longitudinal direction. Thereafter, the outer portions of the slits 400 that are open to the outer surface may be cut by, for example, wire cutting. Alternatively, the whole implant can be made by additive manufacturing, for example by Laser Sintering. In a third alternative, the implant with the cavities is formed by additive manufacturing and the slits are cut by wire cutting, for example.

The slits can also be provided at a portion of the shank that is positioned apart from the tip. For example, the slits can start at a distance from the tip and end at a distance from the head. The position of the slits in the longitudinal direction may vary from one slit to another slit. In use, the slits 400 with the cavities 401 lead to a self-constrained torsional flexibility. When a torsional load acts on the implant, the slits 400 will be closed at a position along the shank where the torsional load becomes too large. This prevents further torsion of the implant.

As in the previously described embodiments, the implant, due to its structure, has at least two stiffness zones in a load versus twisting curve, that is, an initial lower stiffness due to the possible micro-motion that resembles the torsional stiffness of an implant with a smaller diameter, and a subsequent higher torsional stiffness that resembles the torsional stiffness of an implant with a greater diameter. For example, a bone screw of a core diameter of $X_1$, for example 7 mm, may have initially the lower torsional stiffness of a bone screw with a core diameter of $X_2 < X_1$, for example 3.5 mm, when the slit is not yet closed, and may have subsequently upon further twisting the greater torsional stiffness of a bone screw with a core diameter of $X_1$ when the slit is closed.

The implant according to the seventh embodiment can also be a rod or any other implant that may experience torsional loads.

Various other modifications of the embodiments can be contemplated. For example, the implants may be flexible along a length that corresponds only to a portion of the implant, wherein in this case a flexible section is defined by the presence of the cavities and the slits. The implant can also be realized through any bone anchor, with or without a threaded shank, such as a bone nail, for example.

The slits need not have exactly parallel opposing surfaces. It suffices that an abutment takes place when the slit narrows, that prevents or constrains against further flexion.

The interlocking structure of the slit 13', 13", as shown in FIGS. 8 and 9, may be provided for the fourth and fifth embodiments. Features of one embodiment may be combined with features of one or more of the other embodiments.

Instead of the helix-shaped cavities and slits for the bone anchor and the rod, the at least one cavity and the at least one slit may be realized by several annular cavities with annular slits extending around the central axis. Also, the cavities with slits can be axial cavities with axial slits for any of the implants. The cavities with slits can also have interruptions along their length. Furthermore, the shape of the cavity, in particular the depth of the cavity, can vary along a length of the implant. For example, there can be a deep cavity on a first portion of the screw length, such as adjacent to the tip, and a shallow cavity along a second portion of the screw length.

While the implants according to the embodiments shown have a straight shape, in particular in the longitudinal direction, the invention is not limited to implants having a straight shape. For example, the bone plate may have a curvature along its length and/or width and may be formed with an irregular outer contour. For example, a humerus plate may have such a curvature in at least a portion of its length. In addition, also curved rods, straight nails, and curved nails may be contemplated. If the implant has a curvature along at least a portion of its length, the longitudinal axis is defined as a curved central line extending through the implant along its length.

A number of different embodiments are disclosed herein. It is to be appreciated that the different components or methods described with respect to one or more of the different embodiments can be mixed and matched to produce other different embodiments.

What is claimed is:

1. An implant for the stabilization of bones or vertebrae, the implant having a longitudinal axis that extends through a center of the implant and that defines a longitudinal direction, the implant comprising:
    a flexible section having an outer surface, a cavity located near the outer surface and spaced apart from the longitudinal axis, and a slit that connects the cavity with the outer surface in a radial direction relative to the longitudinal axis, wherein a width of the slit in the longitudinal direction is less than a width of the cavity in the longitudinal direction;

wherein the slit forms first opposing wall portions and the cavity forms second opposing wall portions that are located away from the slit, and wherein when a load is applied to the implant in a first direction transverse to the longitudinal axis, the implant is configured to be elastically flexed from a first configuration where the first opposing wall portions are spaced apart from one another and the second opposing wall portions are spaced apart from one another, to a second configuration where, at least on a first side of the implant opposite the application of the load, the first opposing wall portions abut one another such that the flexibility of the implant is limited by the closure of the slit, while a distance that the second opposing wall portions are spaced apart from one another is increased compared to the first configuration.

2. The implant of claim 1, wherein the slit and the cavity each extends continuously around the longitudinal axis from the first side of the implant to an opposite second side of the implant where the load is applied, and wherein when the implant is at the second configuration, on the second side of the implant, a distance that the first opposing wall portions are spaced apart from one another is increased compared to the first configuration, while the distance that the second opposing wall portions are spaced apart from one another is decreased compared to the first configuration.

3. The implant of claim 1, wherein the slit and the cavity on the first side of the implant are a first slit and a first cavity, and wherein a second slit and a second cavity arranged similarly to the first slit and the first cavity are located on an opposite second side of the implant where the load is applied, and wherein when the implant is at the second configuration, on the second side of the implant, a distance that the first opposing wall portions are spaced apart from one another is increased compared to the first configuration, while the distance that the second opposing wall portions are spaced apart from one another is decreased compared to the first configuration.

4. The implant of claim 1, wherein the implant has at least two stiffness zones in a load versus displacement curve, such that a stiffness of the implant is in a first stiffness zone when the implant is at the first configuration, and the stiffness of the implant is in a second stiffness zone that is higher than the first stiffness zone when the implant is at the second configuration and the load remains applied on the implant.

5. The implant of claim 4, wherein the cavity further forms third opposing wall portions separate from the first and second opposing wall portions, wherein both the first opposing wall portions abut one another and the third opposing wall portions abut one another when the stiffness of the implant is in the second stiffness zone, and wherein the stiffness of the implant is in a third stiffness zone that is between the first and second stiffness zones when only one of the first opposing wall portions or the third opposing wall portions abut one another.

6. The implant of claim 1, wherein the first opposing wall portions formed by the slit extend from the cavity to the outer surface in an interlocking manner.

7. The implant of claim 1, wherein the implant comprises a bone anchor.

8. The implant of claim 7, wherein the bone anchor comprises a bone screw with a bone thread, and wherein the slit extends along a root of the bone thread for at least one full turn of the bone thread.

9. The implant of claim 1, wherein the implant comprises a bone plate.

10. The implant of claim 1, wherein when a load is applied to the first side of the implant in a direction opposite the first direction, the implant is configured to be elastically flexed to a third configuration where, at least on the first side of the implant, the second opposing wall portions abut one another to limit the flexibility of the implant, while a distance that the first opposing wall portions are spaced apart from one another is increased compared to the first and second configurations.

11. The implant of claim 1, wherein the first opposing wall portions and the second opposing wall portions extend substantially transverse to the longitudinal axis.

12. The implant of claim 1, wherein in a cross-sectional plane including the longitudinal axis, the cavity has a substantially S-shape or inverted S-shape, with one end of the S-shape or the inverted S-Shape formed by the slit.

13. The implant of claim 1, wherein the cavity further forms third opposing wall portions that are separate from the first and second opposing wall portions and that are configured to abut one another when the implant is flexed from the first configuration towards the second configuration to further limit the flexibility of the implant.

14. The implant of claim 1, wherein the slit is located between the cavity and the outer surface in the radial direction.

15. An implant for the stabilization of bones or vertebrae, the implant having a longitudinal axis that defines a longitudinal direction, the implant comprising:

a flexible section having an outer surface, a cavity located near the outer surface, and a slit that connects the cavity with the outer surface in a radial direction relative to the longitudinal axis, wherein a width of the slit in the longitudinal direction is less than a width of the cavity in the longitudinal direction;

wherein when a load is applied to the implant in a first direction transverse to the longitudinal axis, the implant is configured to be elastically flexed from a first configuration where a stiffness of the implant is in a first stiffness zone to a second configuration where a first abutment increases the stiffness of the implant to a second stiffness zone, and to be further elastically flexed from the second configuration to a third configuration where a second abutment further increases the stiffness of the implant to a third stiffness zone.

16. The implant of claim 15, wherein one of the first or second abutments is between first opposing wall portions formed by the slit, and wherein the other one of the first or second abutments is between second opposing wall portions located away from the slit and formed by the cavity.

17. The implant of claim 16, wherein the slit and the cavity each extends continuously around the longitudinal axis from a first side of the implant to an opposite second side of the implant, and wherein when the load is applied to the second side, the first opposing wall portions formed by the slit are configured to abut one another on the first side while the second opposing wall portions formed by the cavity are configured to abut one another on the second side.

18. The implant of claim 16, wherein the slit and the cavity are formed at least on a first side of the implant, and wherein when the load is applied to an opposite second side of the implant, both the first opposing wall portions formed by the slit are configured to abut one another and the second opposing wall portions formed by the cavity are configured to abut one another on the first side.

19. The implant of claim 16, wherein the slit and the cavity are a first slit and a first cavity located on a first side of the implant, and wherein a second slit and a second cavity arranged similarly to the first slit and the first cavity are located on an opposite second side of the implant, and wherein when the load is applied to the second side, the first opposing wall portions formed by the first slit abut one another on the first side while the second opposing wall portions formed by the second cavity abut one another on the second side.

20. The implant of claim 15, wherein one of the first or second abutments is between first opposing wall portions formed by the slit that are configured to abut one another when a load is applied to the implant in the first direction, and wherein the cavity forms second opposing wall portions located away from the slit that are configured to abut one another when a load is applied to the implant in a direction opposite the first direction.

21. A method of manufacturing an implant for the stabilization of bones or vertebrae, the implant having a longitudinal axis that defines a longitudinal direction and comprising a flexible section having an outer surface, a cavity located near the outer surface, and a slit that connects the cavity with the outer surface in a radial direction relative to the longitudinal axis, wherein a width of the slit in the longitudinal direction is less than a width of the cavity in the longitudinal direction, and wherein when a load is applied to the implant in a first direction transverse to the longitudinal axis, the implant is configured to be elastically flexed from a first configuration where a stiffness of the implant is in a first stiffness zone to a second configuration where a first abutment increases the stiffness of the implant to a second stiffness zone, and to be further elastically flexed from the second configuration to a third configuration where a second abutment further increases the stiffness of the implant to a third stiffness zone, the method comprising:

using an additive manufacturing process to form the implant in a layerwise manner; and forming the cavity in the implant during the additive manufacturing process.

22. The method of claim 21, further comprising forming the slit in the implant during the additive manufacturing process.

23. The method of claim 21, further comprising cutting the implant to form the slit between the cavity and the outer surface after the additive manufacturing process.

* * * * *

UNITED STATES PATENT AND TRADEMARK OFFICE
CERTIFICATE OF CORRECTION

| | |
|---|---|
| PATENT NO. | : 11,583,320 B2 |
| APPLICATION NO. | : 16/804576 |
| DATED | : February 21, 2023 |
| INVENTOR(S) | : Markku Biedermann |

It is certified that error appears in the above-identified patent and that said Letters Patent is hereby corrected as shown below:

In the Specification

Column 4, Line 5     Delete "1" and
                     Insert -- I --

Column 7, Line 14    Delete "12" and
                     Insert -- $I_2$ --

Signed and Sealed this
Sixteenth Day of May, 2023

Katherine Kelly Vidal
*Director of the United States Patent and Trademark Office*